United States Patent [19]

Gäde

[11] 3,944,838
[45] Mar. 16, 1976

[54] ARRANGEMENT FOR PROTECTING THE GONADS IN X-RAY DIAGNOSTICS

[76] Inventor: Ernst-August Gäde, Annastrasse 10, 625 Limburg, Lahn, Germany

[22] Filed: Sept. 6, 1974

[21] Appl. No.: 503,758

[52] U.S. Cl. .................. 250/515; 250/452; 250/456
[51] Int. Cl.² .......................................... G21F 3/00
[58] Field of Search ........... 250/451, 456, 515, 516, 250/519, 452

[30] Foreign Application Priority Data

Sept. 8, 1973  Germany.........................7332714
Feb. 13, 1974  Germany.........................2406717

[56] References Cited
UNITED STATES PATENTS

| | | | |
|---|---|---|---|
| 3,233,248 | 2/1966 | Bushnell | 250/516 X |
| 3,286,094 | 11/1966 | Pretto | 250/519 |
| 3,310,053 | 3/1967 | Greenwood | 250/516 X |
| 3,723,743 | 3/1973 | Brackenbrough et al. | 250/515 |

Primary Examiner—Archie R. Borchelt
Attorney, Agent, or Firm—Craig & Antonelli

[57] ABSTRACT

An arrangement for protecting portions of a person, specifically the gonads, of a person being X-rayed, for use in conjunction with diagnostic X-ray appliances provided with an anti-diffusing screen and a light visor to indicate the object field of the X-rays. The arrangement includes a mounting device which is detachably attachable to the anti-diffusion screen and a shadow-casting plate movably supported by the mounting device. The shadow-casting plate is supported at a support plate made of a material permeable to light and X-rays. The mounting device includes a mounting frame with two spaced longitudinal legs and two spaced cross legs attached to the longitudinal legs, with each of the cross legs including a longitudinal slot for accommodating movable support of the support plate for the shadow-casting device. Leaf springs are provided in the longitudinal slots for holding the support plate in respective adjusted positions, with the support plate being movable both laterally and longitudinally in the slots.

14 Claims, 7 Drawing Figures

ARRANGEMENT FOR PROTECTING THE GONADS IN X-RAY DIAGNOSTICS

The present invention relates to an arrangement for protecting the gonads in X-ray diagnostics for use in connection with diagnostic X-ray appliances provided with an anti-diffusing screen and equipped with a light visor to indicate the object field of the X-rays, with a shadow-casting means movably arranged in a mounting device attachable to the anti-diffusing screen. This shadow-casting means includes a support made of a material permeable to light and X-rays, as well as a plate made of a substance impermeable to light and X-rays.

Due to the strong biological effects of X-rays on man and the dangers connected therewith, it is absolutely necessary to take steps when using the X-rays in the diagnostic and therapeutical fields to provide that the radiation emanating from an X-ray machine can affect only those parts of the human body that must be exposed to the radiation to achieve the desired purpose. However, moreover, it is necessary to protect those body portions within the irradiated zones from direct radiation which are particularly endangered and which need not be exposed to the X-rays.

Therefore, in order to limit the object field of the X-rays, shields of various configurations have been used for a long time, which are placed between the X-ray tube and the patient. Furthermore, for the protection of specific body regions not to be irradiated within the object field, covers of a material impermeable to X-rays have been employed. While the handling of the shields does not cause any difficulties and can readily be executed, the shadowing of body portions is rather problematical under practical conditions, because an exact placing or mounting of the covers intended for this purpose encounters practical difficulties, either because the covers slide off the body, because they do not have the suitable size, or because the X-ray personnel forgets to cover the patient, or considers this step as troublesome and thus omits such covers.

In order to make such covers unnecessary, British Patent No. 918,310 discloses a device for diagnostic X-ray machines consisting essentially of a shadow-casting means made of a material impermeable to X-rays. With the aid of this shadow-casting means, a sharply defined shadow is cast on the zone of the object field not to be irradiated, for example the gonads which are especially sensitive to the effects of X-rays. However, this device can only be employed in X-ray machines equipped with a light visor to indicate the object field of the X-rays. By means of this light visor, with the use of an electric incandescent lamp and a mirror, a light-ray cone is produced coinciding with the X-ray cone, which makes it possible — in addition to the adjustment of the size of the object field by means of screens serving for this purpose — to exactly define the protective shadow cast by the shadow caster. In the device which is arranged to be displaceable with respect to the X-ray tube only in one direction, several impervious, shadow-casting disks are provided on a rotatable, circular plate permeable to light and X-rays, the configuration of these disks corresponding to the body regions to be shadowed. However, in addition to its rather complicated mechanical construction, this apparatus has the disadvantage that, to adjust the shadow to the desired location, namely the patient's gonads, it is not only necessary to effect a longitudinal displacement of the entire apparatus, but also a rotary motion of the plate. This dual movement considerably impedes a rapid and accurate adjustment of the covering shadow, and for this reason this apparatus has found little acceptance in practice, due to resistance encountered with the X-ray personnel and the radiologist.

Therefore, it is an object of the present invention to solve the problem of casting a shadow against X-rays on endangered regions of the human body in a different way and with very minor expenditure, so that the respective adjustment of the shadow can be accomplished accurately and rapidly.

This object is attained, in connection with a device for protecting the gonads in X-ray diagnostics of the aforementioned type, by providing that the mounting means includes a rectangular mounting frame having two longitudinal legs equipped with sliding bars, two cross legs being attached to the longitudinal legs and extending laterally past the latter, each of these cross legs having a longitudinal slot; and that the shadow-casting means is fashioned as a plate which is narrow as compared to the longitudinal slots and can be inserted in these slots and shifted therein. The length of this plate preferably exceeds the length of the longitudinal legs by at least twice such length; and the width of the plate is preferably equal to or only a little smaller than that of the support. This simple device, including two parts, namely the mounting frame and the plate, can be manufactured inexpensively and makes it possible to displace the shadow-casting disk rapidly and exactly so that the shadow can be located at any desired place of the object field.

Suitably, the longitudinal legs of the holding frame are U-shaped rails, the upper U-legs of which serve as sliding bars, the cross legs being attached to the lower U-legs thereof. This arrangement of the longitudinal legs makes it possible to produce the legs from a commercial profile material.

In an advantageous embodiment of this invention, spring elements are disposed in the longitudinal slots. These spring elements serve for fixing the plate in position in any desired location and prevent the shadow-casting means from perhaps falling out of the mounting means when the diagnostic X-ray machine is tilted.

Preferably, leaf springs are used as the spring elements, arranged in the longitudinal direction of the cross legs. However, it is also possible to use a textile fabric with a high pile for such a spring element.

Advantageously, the leaf springs are attached to the topside of the longitudinal slots. This facilitates the introduction of the shadow-casting element into the longitudinal slots.

Another feature of this invention comprises a lead plate of a thickness of between 1 and 2 mm. in the form of a disk, inserted in the support. When using a disk of lead sheet cast into the support, the support can be manufactured as a thin and therefore handy component.

To protect the reproductive glands of male adults and children, the disk suitably has the shape of an asymmetrical oval.

If the gonads of small girls are to be shadowed, the disk is preferably of a heartshape. This disk can also have an approximately triangular configuration in a conventional manner; this contour is best suitable for shadowing the female reproductive organs.

These and other objects, features and advantages of the present invention will become more apparent from the following description when taken in connection with the accompanying drawings which show, for purposes of illustration only, several embodiments in accordance with the present invention.

DETAILED DESCRIPTION OF THE DRAWINGS

Figure 1:
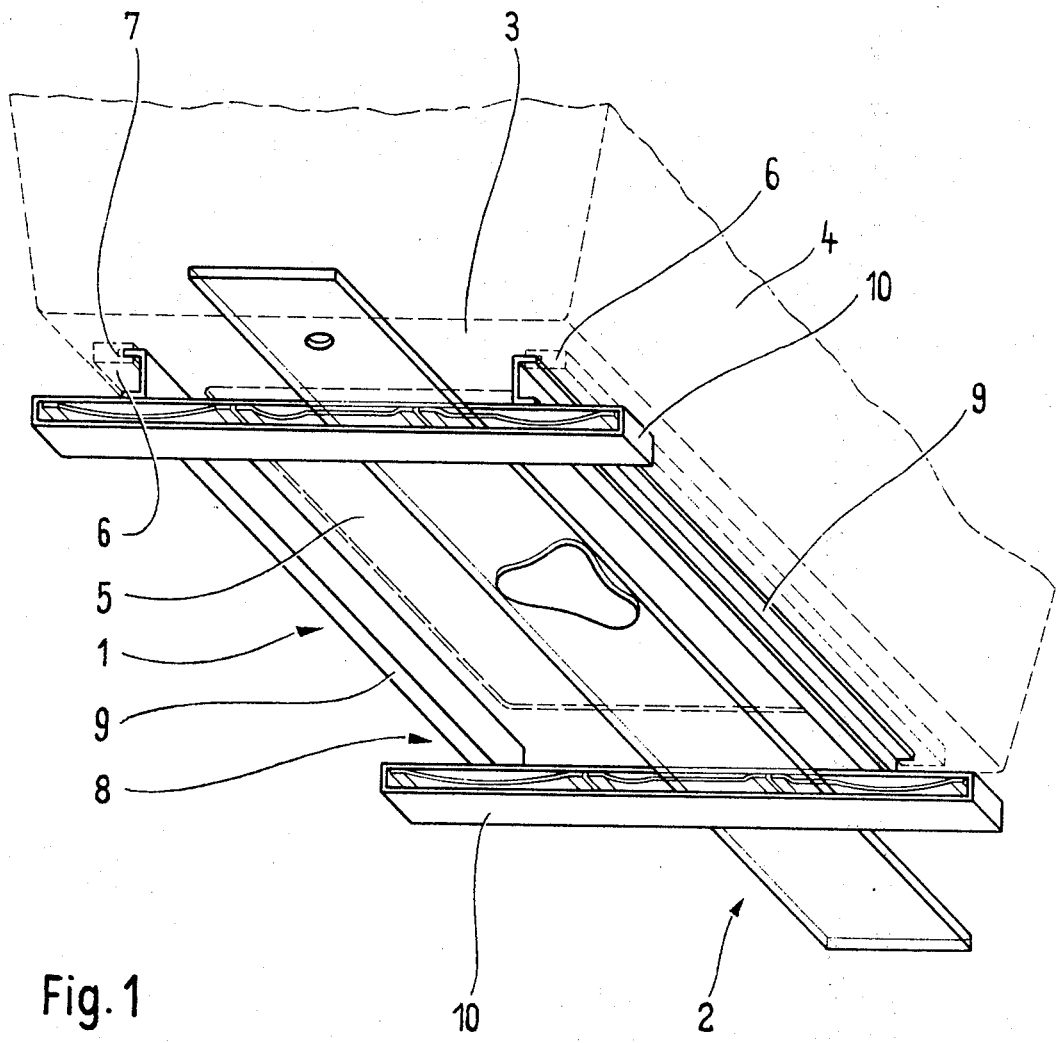
FIG. 1 shows an arrangement in accordance with the present invention mounted to the anti-diffusing screen of a diagnostic X-ray machine, in a perspective view seen obliquely from below.

The proposed device for protecting the gonads in X-ray diagnostics is bipartite and includes a mounting device 1, as well as a shadow-casting means 2. The holder 1 is arranged on the underside 3 of an anti-diffusing screen 4 (indicated by dashed lines) of a diagnostic X-ray machine, having a rectangular opening 5 for the exit of X-rays. Insert rails 6 (likewise indicated by dashed lines) are disposed on two sides of the opening 5, provided by the manufacturer of the diagnostic X-ray machine for the mounting of screens, tubes, and filters and having a longitudinal groove 7. To fix the aforementioned accessory elements in position, a spring clip (not shown) is provided on one of the two insert rails 6.

Figure 2:
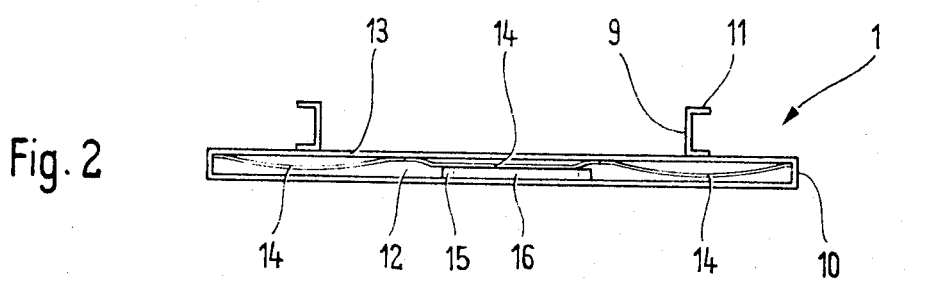
FIG. 2 shows the arrangement according to FIG. 1 in a front view.

The mounting element 1 is — as can be seen in FIG. 1 — a rectangular mounting frame 8 composed essentially of two longitudinal legs 9 and two cross legs 10. The longitudinal legs 9 of the holding frame 8 are (see FIG. 2) U-shaped rails made, for example, of aluminum, the upper U-legs of which serve as sliding bars 11 seated in the longitudinal grooves 7 of the insert rails 6. The two cross legs 10, which can likewise be made of aluminum, are mounted to the lower U-legs of the U-shaped rails.

The two cross legs 10 laterally project beyond the longitudinal legs 9 by a portion corresponding to about one-fifth of their length. These cross legs are provided each with a longitudinal slot 12, extending over the entire length thereof. The shape of a cross leg 10 accordingly corresponds to that of a long, narrow and high box, open on the topside and bottom side.

In the interior of the cross legs 10, along the cover 13 of the longitudinal slots 12 facing the longitudinal legs 9, three spring elements are arranged in the form of leaf springs 14 which are attached, for example, by means of rivets (not shown) to the cross leg 10 and are disposed in series in the direction of the cross legs 10.

Figure 3:
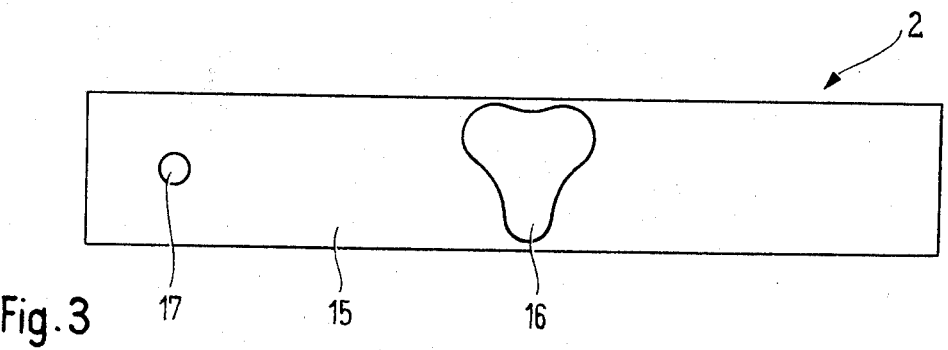
FIG. 3 shows the shadow-casting element according to FIG. 1 in a plan view.

The shadow-casting means 2 (see FIG. 3) consists of a plate-shaped support 15 of a material permeable to light and X-rays, as well as a disk 16 made of a substance impermeable to light rays as well as X-rays.

The width of the support 15 corresponds approximately to one-fourth of the length of a longitudinal slot 12, and the support 15 is approximately twice as long as one longitudinal leg 9, see FIG. 1. The thickness of the support 15 occupies about half the height (thickness) of a longitudinal slot 12. The width of the plate 16 is only a little less than that of the support 15, see FIG. 3. The plate 16 is cast into the support 15. The support 15 can be made, for example, of acrylic glass, whereas the plate 16 is a lead plate having a thickness of 1–2 mm.

The shadow-casting element 2 is (see FIGS. 1 and 2) inserted in the longitudinal slots 12 of the cross legs 10 and fixed in position with the aid of the leaf springs 14. A hole 17 arranged in the proximity of one end of the shadow-casting means 2 permits the hanging of the appliance during nonuse on a hook.

Figure 4:
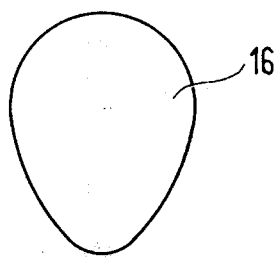
FIG. 4 shows a plate intended for male adults.
Figure 5:
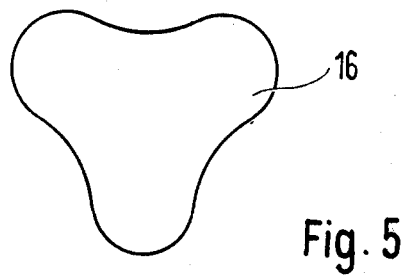
FIG. 5 shows a plate intended for female adults.
Figure 6:
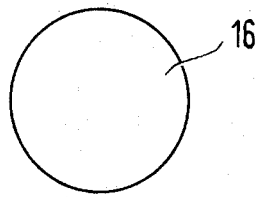
FIG. 6 shows a plate suitable for male children.
Figure 7:
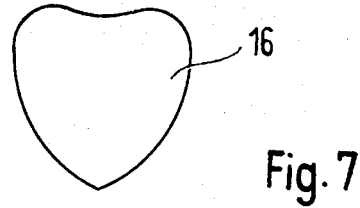
FIG. 7 shows a plate suitable for female children.

Each device of this invention includes four shadow-casting means 2, equipped with plates 16 of varying contours. The disk 16 according to FIG. 4 is utilized to protect the gonads of male adults, while the plate 16 according to FIG. 5 serves to protect the female reproductive glands, and the disk 16 according to FIG. 6 is used in male children, while the plate 16 in FIG. 7 is utilized for female children.

The operation of the device of this invention is simple. First of all, the mounting means 1 is attached to the anti-diffusing screen 4 of the diagnostic X-ray apparatus, by inserting the sliding bars 11 of the longitudinal legs 9 of the mounting frame 8 in the longitudinal grooves 7 of the insert rails 6, until they are arrested therein by means of the spring clip. With the light visor being switched on, the patient's position with respect to the X-ray object field is first determined, and then the shadow-casting means 2 with a plate 16 according to FIGS. 4 – 7, intended for the patient (male, female, child) is inserted in the longitudinal slots 12 and displaced therein until the gonads are shadowed. Thereafter, the X-ray photograph is made, the plate 16 masking the X-ray cone oriented toward the reproductive glands.

While I have shown and described several embodiments in accordance with the present invention, it is understood that the same is not limited thereto but is susceptible of numerous changes and modifications as known to those skilled in the art, and I therefore do not wish to be limited to the details shown and described herein but intend to cover all such changes and modifications as are encompassed by the scope of the appended claims.

What is claimed is:

1. Arrangement for protecting the gonads in X-ray diagnostics for use in connection with diagnostic X-ray appliances provided with an anti-diffusing screen and equipped with a light visor to indicate the object field of the X-rays, with a shadow-casting means movably arranged in a mounting device attachable to the anti-diffusing screen, this shadow-casting means including a support made of a material permeable to light and X-rays, as well as a plate made of a substance impermeable to light and X-rays, characterized in that the mounting device includes a rectangular mounting frame having two longitudinal legs provided with sliding bars, to which two cross legs are attached which laterally project beyond the longitudinal legs and are provided each with a longitudinal slot; and that the shadow-casting means is fashioned as a plate narrow as compared to the longitudinal slots, which plate can be inserted and displaced in these longitudinal slots, the length of this plate exceeding that of the longitudinal legs by at least twice such length; and that the width of the plate is equal to or little smaller than that of the support.

2. Arrangement according to claim 1, characterized in that the longitudinal legs of the mounting frame are U-shaped rails, the upper U-legs of which serve as sliding bars and the cross legs being attached to the lower U-legs thereof.

3. Arrangement according to claim 1, characterized in that spring elements are disposed in the longitudinal slots.

4. Arrangement according to claim 3, characterized in that leaf springs serve as the spring elements, which extend in the longitudinal direction of the cross legs.

5. Arrangement according to claim 4, characterized in that the leaf springs are attached to the cover of the longitudinal slots.

6. Arrangement according to claim 1, characterized by a lead plate inserted in the support, this plate having a thickness of between 1 and 2 millimeters and constituting a disk.

7. Arrangement according to claim 1, characterized in that the plate corresponds to an asymmetrical oval.

8. Arrangement according to claim 1, characterized in that the plate is heart-shaped.

9. Arrangement according to claim 1, characterized in that the plate has an approximately triangular configuration.

10. Arrangement according to claim 2, characterized in that spring elements are disposed in the longitudinal slots.

11. An arrangement for protecting portions of a person being X-rayed for use in connection with diagnostic X-ray appliances provided with an anti-diffusing screen and a light visor to indicate the object field of the X-rays; said arrangement comprising:

a mounting device which is attachable to the anti-diffusing screen, a shadow-casting means movably supported by said mounting device, said shadow-casting means including a support made of a material permeable to light and X-rays and a shadow plate made of a substance impermeable to light and X-rays, wherein the mounting device includes a mounting frame with two spaced longitudinal legs and at least one cross leg attached to said longitudinal legs, each of said at least one cross legs being provided with a longitudinal slot therethrough, wherein said support of said shadow-casting means is fashioned as a support plate which has a lateral dimension less than the lateral dimension of the respective slots in said cross legs, said support plate being insertable in and displaceable both longitudinally and laterally in said slots, and wherein resilient means are provided in said slots for maintaining said support plate in respective adjusted positions.

12. An arrangement according to claim 11, wherein the mounting frame includes two of said cross legs at respective opposite ends of the longitudinal legs, and wherein said support plate is approximately twice as long as the longitudinal legs.

13. An arrangement according to claim 12, wherein the shadow plate has a lateral width no greater than the lateral width of the support plate.

14. An arrangement according to claim 11, wherein said spring means includes leaf springs extending substantially across the lateral width of said slots.

* * * * *